US008858983B2

(12) United States Patent
Burgmeier

(10) Patent No.: US 8,858,983 B2
(45) Date of Patent: Oct. 14, 2014

(54) ANTIOXIDANTS AND ANTIMICROBIAL ACCESSORIES INCLUDING ANTIOXIDANTS

(75) Inventor: Robert E. Burgmeier, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 413 days.

(21) Appl. No.: 12/725,072

(22) Filed: Mar. 16, 2010

(65) Prior Publication Data
US 2010/0278894 A1   Nov. 4, 2010

Related U.S. Application Data

(60) Provisional application No. 61/174,349, filed on Apr. 30, 2009, provisional application No. 61/174,411, filed on Apr. 30, 2009.

(51) Int. Cl.
| A61F 2/00 | (2006.01) |
| A61K 9/00 | (2006.01) |
| A61K 38/12 | (2006.01) |
| A61K 31/7028 | (2006.01) |
| A61K 31/7036 | (2006.01) |
| A61K 31/65 | (2006.01) |
| A61P 41/00 | (2006.01) |
| A61P 31/04 | (2006.01) |
| A61P 43/00 | (2006.01) |
| A61L 27/18 | (2006.01) |
| A61L 27/54 | (2006.01) |

(52) U.S. Cl.
CPC ............ *A61L 27/54* (2013.01); *A61L 2300/254* (2013.01); *A61L 2300/40* (2013.01); *A61L 27/18* (2013.01); *A61L 2300/61* (2013.01); *A61L 2300/404* (2013.01)
USPC .............................. 424/426; 424/423; 424/400

(58) Field of Classification Search
USPC ....................................................... 424/423
See application file for complete search history.

(56) References Cited

U.S. PATENT DOCUMENTS

| 4,226,848 | A | 10/1980 | Nagai et al. |
| 4,917,686 | A | 4/1990 | Bayston et al. |
| 4,968,539 | A | 11/1990 | Aoyagi et al. |
| 5,217,493 | A | 6/1993 | Raad et al. |
| H1465 | H | 7/1995 | Stokes |
| 5,447,724 | A | 9/1995 | Helmus et al. |
| 5,624,704 | A | 4/1997 | Darouiche et al. |
| 5,722,992 | A | 3/1998 | Goldmann |
| 5,756,145 | A | 5/1998 | Darouiche |
| 5,766,248 | A | 6/1998 | Donovan |
| 5,856,367 | A | 1/1999 | Barrows et al. |
| 5,897,590 | A | 4/1999 | Donovan |
| 5,902,283 | A | 5/1999 | Darouiche et al. |
| 6,099,562 | A | 8/2000 | Ding et al. |
| 6,162,487 | A | 12/2000 | Darouiche |
| 6,275,728 | B1 | 8/2001 | Venkatraman et al. |
| 6,284,305 | B1 | 9/2001 | Ding et al. |
| 6,319,512 | B1 | 11/2001 | Rothen-Weinhold et al. |
| 6,475,434 | B1 | 11/2002 | Darouiche et al. |
| 6,562,363 | B1 | 5/2003 | Mantelle et al. |
| 6,599,275 | B1 | 7/2003 | Fischer, Jr. |
| 6,635,078 | B1 * | 10/2003 | Zhong et al. ................. 623/1.11 |
| 6,663,662 | B2 | 12/2003 | Pacetti et al. |
| 6,855,777 | B2 | 2/2005 | McLoughlin et al. |
| 6,887,270 | B2 | 5/2005 | Miller et al. |
| 6,933,026 | B2 | 8/2005 | Mauze et al. |
| 6,949,254 | B2 | 9/2005 | Gen |
| 6,968,234 | B2 | 11/2005 | Stokes |
| 7,063,682 | B1 | 6/2006 | Whayne et al. |
| 7,245,973 | B2 | 7/2007 | Liu et al. |
| 7,390,523 | B2 | 6/2008 | Pacetti et al. |
| 7,410,497 | B2 | 8/2008 | Hastings et al. |
| 7,419,709 | B2 | 9/2008 | Rypacek et al. |
| 7,534,241 | B2 | 5/2009 | Coppeta et al. |
| 7,596,408 | B2 | 9/2009 | Singhal et al. |
| 7,621,906 | B2 | 11/2009 | Pastore et al. |

(Continued)

FOREIGN PATENT DOCUMENTS

| CN | 1984686 A | 6/2007 |
| EP | 0640661 A2 | 3/1995 |

(Continued)

OTHER PUBLICATIONS

U.S. Appl. No. 12/725,083, by Robert E. Burgmeier, filed Mar. 16, 2010.

(Continued)

*Primary Examiner* — Walter Webb
(74) *Attorney, Agent, or Firm* — Shumaker & Sieffert, P.A.

(57) ABSTRACT

An antimicrobial accessory may include a polymer an antimicrobial mixed in the polymer, and an antioxidant. The antioxidant may include, for example, at least one of citric acid, maltol, kojic acid, malic acid, or vitamin A. In some examples, the antioxidant may include an ascorbate peroxidase in combination with ascorbic acid, a glutathione peroxidase in combination with glutathione, or a superoxide dismutase in combination with a metal such as Ni, Cu, Mn, or Fe. In some examples, the antimicrobial accessory may include at least three polymer layers. For example, the antimicrobial accessory may include a first layer comprising a biodegradable polymer and an antimicrobial. The antimicrobial accessory may further include a sacrificial diffusion layer formed on a surface of the first layer. The sacrificial diffusion layer may include a biodegradable polymer, which may be the same biodegradable polymer as in the first layer or may be a different biodegradable polymer. The antimicrobial accessory may also include a topcoat formed on the sacrificial diffusion layer. The topcoat may include a biodegradable polymer and at least one antioxidant mixed in the biodegradable polymer.

16 Claims, 5 Drawing Sheets

(56) References Cited

U.S. PATENT DOCUMENTS

| | | |
|---|---|---|
| 7,622,146 B2 | 11/2009 | Roorda et al. |
| 2003/0086963 A1 | 5/2003 | Scamilla Aledo et al. |
| 2003/0143256 A1 | 7/2003 | Gen |
| 2003/0161870 A1 | 8/2003 | Hsu et al. |
| 2003/0203015 A1 | 10/2003 | Aledo et al. |
| 2003/0204239 A1 | 10/2003 | Carlyle et al. |
| 2004/0048016 A1 | 3/2004 | Wang et al. |
| 2004/0186528 A1 | 9/2004 | Ries et al. |
| 2005/0037052 A1 | 2/2005 | Udipi et al. |
| 2005/0079199 A1 | 4/2005 | Heruth et al. |
| 2005/0244453 A1* | 11/2005 | Stucke et al. ............ 424/423 |
| 2005/0267543 A1 | 12/2005 | Heruth et al. |
| 2005/0271701 A1 | 12/2005 | Cottone, Jr. et al. |
| 2006/0009806 A1 | 1/2006 | Heruth et al. |
| 2006/0039946 A1 | 2/2006 | Heruth et al. |
| 2006/0051392 A1 | 3/2006 | Heruth et al. |
| 2006/0051393 A1 | 3/2006 | Heruth et al. |
| 2006/0095020 A1 | 5/2006 | Casas et al. |
| 2006/0216403 A1* | 9/2006 | Hayes ............................ 427/2.1 |
| 2006/0240065 A1 | 10/2006 | Chen |
| 2007/0010632 A1* | 1/2007 | Kaplan et al. ............ 525/423 |
| 2007/0198063 A1 | 8/2007 | Hunter et al. |
| 2007/0212381 A1 | 9/2007 | DiFiore et al. |
| 2008/0014236 A1 | 1/2008 | Pacetti et al. |
| 2008/0014245 A1 | 1/2008 | Pacetti et al. |
| 2008/0075628 A1 | 3/2008 | Judd et al. |
| 2008/0125728 A1 | 5/2008 | Bischoff et al. |
| 2008/0128315 A1 | 6/2008 | Buevich et al. |
| 2008/0132922 A1 | 6/2008 | Buevich et al. |
| 2008/0208325 A1 | 8/2008 | Helmus et al. |
| 2008/0241212 A1 | 10/2008 | Moses et al. |
| 2008/0241245 A1 | 10/2008 | Myers et al. |
| 2008/0243241 A1 | 10/2008 | Zhao |
| 2008/0260796 A1 | 10/2008 | Bischoff et al. |
| 2009/0041824 A1 | 2/2009 | Zugates et al. |
| 2009/0081272 A1 | 3/2009 | Clarke et al. |
| 2009/0198063 A1 | 8/2009 | Kiyoto et al. |
| 2009/0198197 A1 | 8/2009 | Bischoff et al. |
| 2009/0280153 A1 | 11/2009 | Hunter et al. |
| 2009/0292327 A1 | 11/2009 | Singhal et al. |
| 2010/0158970 A1 | 6/2010 | Tipton et al. |
| 2010/0198278 A1 | 8/2010 | Cobian et al. |
| 2010/0203100 A1 | 8/2010 | Cobian et al. |
| 2010/0278895 A1 | 11/2010 | Burgmeier |
| 2012/0165795 A1 | 6/2012 | Seiler et al. |

FOREIGN PATENT DOCUMENTS

| | | |
|---|---|---|
| EP | 2016939 A1 | 1/2009 |
| WO | WO 95/05138 A1 | 2/1995 |
| WO | WO 96/39215 A1 | 12/1996 |
| WO | WO 98/15317 A1 | 4/1998 |
| WO | WO 01/64258 A1 | 9/2001 |
| WO | WO 01/66159 A1 | 9/2001 |
| WO | WO 01/66162 A1 | 9/2001 |
| WO | WO 02/05788 A1 | 1/2002 |
| WO | WO 02/13783 A2 | 2/2002 |
| WO | WO 03/000156 A1 | 1/2003 |
| WO | WO 03/028660 A2 | 4/2003 |
| WO | WO 2004/026361 A1 | 4/2004 |
| WO | WO 2004/084955 A1 | 10/2004 |
| WO | 2005007035 A1 | 1/2005 |
| WO | WO 2005/000268 A1 | 1/2005 |
| WO | WO 2005/051234 A2 | 6/2005 |
| WO | WO 2005/058414 A1 | 6/2005 |
| WO | 2005061003 A1 | 7/2005 |
| WO | WO 2005/072703 A2 | 8/2005 |
| WO | WO 2006/039330 A1 | 4/2006 |
| WO | WO 2008/024149 A2 | 2/2008 |
| WO | WO 2008/027783 A2 | 3/2008 |
| WO | WO 2008/039917 A2 | 4/2008 |
| WO | WO 2008/039923 A2 | 4/2008 |
| WO | WO 2008/117268 A2 | 10/2008 |
| WO | WO 2008/131089 A2 | 10/2008 |
| WO | WO 2010/088682 A2 | 8/2010 |
| WO | WO 2010/088697 A2 | 8/2010 |

OTHER PUBLICATIONS

Notification of Transmittal of the International Search Report and the Written Opinion of the International Searching Authority for patent application No. PCT/US2010/027891, mailed Dec. 21, 2010, 11 pages.

Notification of Transmittal of the International Search Report and the Written Opinion of the International Searching Authority for patent application No. PCT/US2010/027890, mailed Dec. 21, 2010, 13 pages.

Non-final office action for U.S. Appl. No. 12/725,083, mailed Mar. 29, 2012, 10 pages.

Kuhn et al., "Antimicrobial Implant Coating in Arthroplasty," Local Antibiotics in Arthroplasty (ISBN 9783131346414). 2007, pp. 23-29.

Vogt et al., "Resorbable Antibiotic Coatings for Bone Substitutes and Implantable Devices," Mat-wiss u. Werkstofftech, 2005, 36, No. 12, pp. 814-819.

Vogt et al., "Design of an Antibiotic Delivery System Based on a Bioresorbable Bone Substitute," Advanced Engineering Materials 2007, 9, No. 12, pp. 1135-1140.

Stemberger et al., "New Antibiotic Carriers and Coatings in Surgery," Local Antibiotics in Arthroplasty (ISBN 9783131346414), 2007, pp. 13-21.

Mizrahi et al., "Adhesive Tablet Effective for Treating Canker Sores in Humans," Journal of Pharmaceutical Sciences, vol. 93, No. 12, Dec. 2004, pp. 2927-2935.

Matl, "New Anti-Infective Coatings of Medical Implants," Antimicrobial Agents and Chemotherapy, vol. 52, No. 6, Jun. 2008, pp. 1957-1963.

Letsch et al., "Local antibiotic administration in osteomyelitis treatment—a comparative study with two different carrier substances," Aktuelle Traumatol, Nov. 1993, 23(7): 324-9 (translation of abstract included).

Von Hasselbach et al., "Clinical aspects and pharmacokinetics of collagen-gentamicin as adjuvant therapy of osseous infections," Unfallchirurg, Sep. 1989, 92(9):459-70 (English translation of abstract included).

Hettfleisch et al., "Release of gentamicin from biomaterials implanted into the lumen of intermedullary local carriers—a pharmacokinetic study," Aktuelle Traumatol, Apr. 1993, 23(2): 68-71 (translation of abstract included).

Attmanspacher et al., "Medium-term results in the treatment of postoperative septic arthritis of the shoulder," Unfallchirurg Springier-Verlag, 2000, 103:1048-1056.

"CollaRx® Gentamicin Surgical Implant: Ex-US," http://www.innocollinc.com/index.php/CollaRx-Gentamicin-Surgical-Implant—Ex-US.html, accessed on Jun. 16, 2009, 3 pp.

Ipsen et al., "Gentamicin-collagen sponge for local applications," Acta Orthop Scand, Dec. 1991, 62(6):592-4.

Jerosch et al., "Septic Arthritis: Arthroscopic Management With Local Antibiotic Treatment," Acta Orthopaedica Belgica, 1995, 61 (2): 126-34.

Jerosch et al., "Arthroscopic treatment of Septic Arthritis-Surgical Technique," Unfallchirurg, Jun. 1998, 101(6):454-60 (translation of abstract included).

Eklund, "Prevention of sternal wound infections with locally administered gentamicin," APMIS 115:1022-1024, 2007.

Gomez et al., "Effectiveness of collagen-gentamicin implant for treatment of 'dirty' abdominal wounds," World J Surg, 1999; 23: 123-127 (translation of abstract included).

Musella et al., "Collagen tampons as aminoglycoside carriers to reduce postoperative infection rate in prosthetic repair of groin hernias," Eur J Surg, Feb. 2001;167(2):130-2.

Nowacki et al., "Prospective, randomized trial examining the role of gentamycin-containing collagen sponge in the reduction of postoperative morbidity in rectal cancer patients: early results and surprising outcome at 3-year follow-up," Int J Colorectal Dis, 2005; 20:114-120.

(56) References Cited

OTHER PUBLICATIONS

Rutten et al., "Prevention of wound infection in elective colorectal surgery by local application of gentamicin-containing collagen sponge," Eur J Surg Suppl, 1997; (578):31-5.
Vogel et al., "Treatment of pilonidal sinus with excision and primary suture using a local, resorbable antibiotic carrier. Results of a randomized prospective study," Chirurg, 1992; Sep;63(9):748-53 (translation of abstract included).
Stemberger et al., "Local treatment of bone and soft tissue infections with collagen-gentamicin sponge," Eur J Surg Suppl, 1997; 578:17-26.
Nielsen et al., "Contaminated fistula following J-pouch ileoanal reservoir (Case Report)," Eur J Surg, Mar. 1991; 157(3):219-20.
Kallehave et al., "Topical antibiotics used in the treatment of complex wounds: A discussion of the use of collagen sponges impregnated with gentamicin in the treatment of six patients with complicated, infected, soft tissue wounds following gastrointestinal surgery," Journal of Wound Care. 1996; vol. 5, No. 4, pp. 155-160.
Lampe et al., "Necrosectomy with an Ultrasonic Dissector in the Treatment of Necrotizing Pancreatitis," Acta Chir Bleg, 2006; vol. 106, 177-180.
Meyer et al., "Perineal wound closure after abdominal-perineal excision of the rectum," Tech Coloproctol, 2004; 8:s230-s234.
Leyh et al., "Adjuvant treatment of deep sternal wound infections with collagenous gentamicin," Ann Thorac Surg, Nov. 1999;68(5): 1648-51.
Eklund el al., "Prophylaxis of sternal wound infections with gentamicin-collagen implant: randomized controlled study in cardiac surgery," Journal of Hospital Infection, 2005; 59:108-112 (translation of abstract included).
Friberg et al., "Antibiotic concentrations in serum and wound fluid after local gentamicin or intravenous dicloxacillin prophylaxis in cardiac surgery," Scand J Infect Dis, 2003; 35(4):251-4.
Friberg el al., "Local gentamicin reduces the sternal wound infections after cardiac surgery: a randomized controlled trial," Ann Thorac Surg, Jan. 2005;79(1): 153-61.
Friberg et al., "Cost effectiveness of local collagen gentamicin as prophylaxis for sternal wound infections in different risk groups," Scandinavian Cardiovascular Journal, 40, 2006, pp. 117-125.
Friberg et al., "Influence of more than six sternal fixation wires on the incidence of deep sternal would infection," Thioac Cardiov Surg, 2006; 54:468-473.
Friberg et al., "Incidence, microbiological findings , and clinical presentation of sternal wound infections after cardiac surgery with and without gentamicin prophylaxis," Eur J Clin Microbiol Infect Dis, 2007; 26: 91-97.
Horch et al., "Prevention of infection in Teflon prostheses for dialysis access: experiences with a resorbable combined collagen-antibiotic system," Vasa, 1989; 18(1):30-4 (English translation of abstract included).
Jorgensen et al., "Clinical and pharmacokinetic evaluation of gentamicin-containing collagen in groin wound infections after vascular reconstruction," Eur J Vasc Surg, Feb. 1991; 5(1):87-91.
Belz et al., "Use of gentamicin-collagen fleece in vascular surgery," Angio, 1989: 11(14): 147-152 (translation of abstract included).
Holdsworth, "Treatment of infective and potentially infective complications of vascular bypass grafting using gentamicin with collagen sponge," Ann R Coll Surg Engl, May 1999; 81(3): 166-70.
Rohde, "Spondylodiscitis after Lumbar Discectomy: Incidence and a Proposal for Prophylaxis," Spine, 1998; vol. 23, No. 5, pp. 615-620.
Kolodziejcyk, "Epidural 'Sulmycin Implant'—coverage of local infection prophylaxis in surgical treatment of penetrating head injuries," Akt Traumatol, 1992; 22: 272-275 (translation of abstract included).
Zink et al., "Prophylaxis of postoperative lumbar spondylodiscitis," Neurosurg Rev, 1989; 12(4): 297-303.
Arlt el al., "Diabetic Foot," Langenbecks Arch Chir, 1997; Suppl II, pp. 528-532 (English translation of abstract included).
Faludi et al., "Experience Acquired by Applying Gentamicin-Sponge," Acta Chirurgica Hungarcia, 1997; 36(14): 81-82.
Kwasny et al., "The use of gentamicin collagen floss in the treatment of infections in trauma surgery," Orthopedics, May 1994, 17(5):421-425.
Castor, "Local Antibiotic Therapy via a Fistula: Treatment of a Postoperative Abscess with Collagen and Gentamicin," Scand J Infect, 1999; 31:216.
Schafer et al., "Is the Primary Suture Indicated in Infected Wounds in Pediatric Surgery," Langenbecks Arch Chir Supp II, Kongrebeacht, 1997; 1, pp. 1350-1352 (translation of abstract included).
Friberg, "Local collagen-gentamicin for prevention of sternal wound infections: the LOGIP trial," APMIS 115: 1016-21, 2007.
Friberg et al, "Collagen-gentamicin for prevention of sternal wound infection; long-term follow-up of effectiveness," Interactive CardioVascular and Thoracic Surgery, 9(2009):454-458.
Peerdeman et al., "In situ treatment of an infected intrathecal baclofen pump implant with gentamicin-impregnated collagen fleece," Technical note, J Neurosurg, Sep. 4, 2009, pp. 1-3.
Rusczak et al., "Collagen as a carrier for on-site delivery of antibacterial drugs," Advanced Drug Delivery Reviews 55, 2003, 1679-1698.
Dernevik, "Infection Rates After Pacemaker Operations and Prophylaxis with Gentamicin-Collagen Patches in the Generation Pocket," Europace, vol. 4, (Supplemental 2), Dec. 2003, 2 pp.
Wachol-Drewek, "Comparative Investigation of Drug Delivery Collagen Implants Saturated in Antibiotic Solutions and a Sponge Containing Gentamicin," Biomaterials, vol. 17, No. 17, Oct. 20, 1995, 1733-1738, 6 pp.
Petrie et al., "Pressure Sensitive Adhesives for Health Care," dated Jun. 4, 2004, 2 pp.
TyRx Pharma, Inc. Announces Food and Drug Administration (FDA) 510(k) Clearance of the AIGIS (Rx) (TM) Cardiac Rhythm Medical Device (CRMD) Anti-Bacterial Envelope, an Innovative Mesh Envelope Designed to Immobilize and Reduce Bacterial Infection of a Pacemaker or Implantable Cardioverter Defibrillator (ICD) When Implanted in the Body, Market Wire, Jan. 2008, 2 pp.

* cited by examiner

ANTIOXIDANTS AND ANTIMICROBIAL ACCESSORIES INCLUDING ANTIOXIDANTS

This application claims the benefit of U.S. Provisional Application No. 61/174,349, entitled, "ANTIOXIDANTS AND ANTIMICROBIAL ACCESSORIES INCLUDING ANTIOXIDANTS," filed on Apr. 30, 2009, and U.S. Provisional Application No. 61/174,411, entitled, "ANTIOXIDANTS AND ANTIMICROBIAL ACCESSORIES INCLUDING ANTIOXIDANTS," filed on Apr. 30, 2009, the entire contents of which are incorporated herein by reference.

TECHNICAL FIELD

The disclosure relates to implantable medical devices and, more particularly, to methods of reducing risk of post-implantation infection.

BACKGROUND

Implantable medical devices (IMDs) include a variety of devices that provide therapy (such as electrical stimulation or drug delivery) to a patient, monitor a physiological parameter of a patient, or both. IMDs typically include a number of functional components encased in a housing. An IMD may also include a lead or catheter extending from the housing. The housing and lead or catheter is implanted in a body of the patient. For example, the housing may be implanted in a pocket created in a torso of a patient. The housing, lead, and/or catheter may be constructed of biocompatible materials, such as titanium, silicone, polyurethane, or the like. While the housing, lead and catheter are biocompatible, there may still be a risk of infection to the patient as a result of the implantation procedure or the presence of the IMD in the body.

SUMMARY

In general, the disclosure is directed to an antimicrobial accessory for use with an implantable medical device (IMD). The antimicrobial accessory may be configured to be attached to or implanted adjacent to the IMD to reduce or substantially eliminate risk of post-implant infection to a patient in which the IMD is implanted. In some examples, the antimicrobial accessory may be formed integrally with the IMD, such as a housing of the IMD, a lead body, or a catheter.

The antimicrobial accessory may include a polymer, an antimicrobial mixed in the polymer, and an antioxidant mixed in the polymer. The antioxidant may generally be a naturally occurring compound with antioxidant properties. The antioxidant may include multiple conjugated double bonds, e.g., may be a highly conjugated compound, may be a relatively low molecular weight compound, or both. For example, the antioxidant may include at least one of citric acid, maltol, kojic acid, malic acid, or vitamin A. When an antioxidant compound is highly conjugated and relatively low molecular weight, the antioxidant may be an efficient electron or free radical scavenger on a per weight basis. Additionally, an antioxidant having a relatively low molecular weight may facilitate mixing of the antioxidant into the polymer. In some embodiments, the antioxidant includes an enzyme and a substrate on which the enzyme acts, such as, for example, an ascorbate peroxidase in combination with ascorbic acid, a glutathione peroxidase in combination with glutathione, or a superoxide dismutase in combination with a metal such as Ni, Cu, Mn, or Fe. The enzyme catalyzes oxidation of the substrate, and may provide improved oxidation protection to the polymer and/or antimicrobial than an antioxidant substrate alone.

In some examples, the antimicrobial accessory may include multiple layers. For example, the antimicrobial accessory may include a first layer comprising a biodegradable polymer and an antimicrobial. The antimicrobial accessory may further include a sacrificial diffusion layer formed on a surface of the first layer. The sacrificial diffusion layer may include a biodegradable polymer, which may be the same biodegradable polymer as in the first layer or may be a different biodegradable polymer. The antimicrobial accessory may also include a topcoat formed on the sacrificial diffusion layer. The topcoat includes a biodegradable polymer and an antioxidant.

The sacrificial diffusion layer may reduce or substantially eliminate contamination of the antimicrobial disposed in the first layer with the antioxidant or impurities formed from oxidation of the antioxidant disposed in the topcoat. At least one of the thickness of the sacrificial diffusion layer and the material from which the sacrificial diffusion layer is formed may be selected so that the topcoat and sacrificial diffusion layer degrade before mixing of the antioxidant and the antimicrobial occurs in the sacrificial diffusion layer.

In one aspect, the disclosure is directed to an antimicrobial accessory comprising a first layer including a first biodegradable polymer and an antimicrobial, a sacrificial diffusion layer formed on the first layer, and a topcoat formed on the sacrificial diffusion layer. According to this aspect of the disclosure, the sacrificial diffusion layer comprises a second biodegradable polymer, and the topcoat comprises a third biodegradable polymer and an antioxidant.

In another aspect, the disclosure is directed to a system including an implantable medical device and an antimicrobial accessory. According to this aspect of the disclosure, the antimicrobial accessory may include a first layer comprising a first biodegradable polymer and an antimicrobial, a sacrificial diffusion layer formed on the first layer, and a topcoat formed on the sacrificial diffusion layer. The sacrificial diffusion layer comprises a second biodegradable polymer, and the topcoat comprises a third biodegradable polymer and an antioxidant.

In an additional aspect, the disclosure is directed to a method of forming an antimicrobial accessory. The method includes forming a first layer comprising a first biodegradable polymer and an antimicrobial, forming a sacrificial diffusion layer on a surface of the first layer, and forming a topcoat on a surface of the sacrificial diffusion layer. The sacrificial diffusion layer may include a second biodegradable polymer, and the topcoat may include a third biodegradable polymer and an antioxidant.

The details of one or more examples of the disclosure are set forth in the accompanying drawings and the description below. Other features, objects, and advantages of the disclosure will be apparent from the description and drawings, and from the claims.

DETAILED DESCRIPTION

Figure 1:
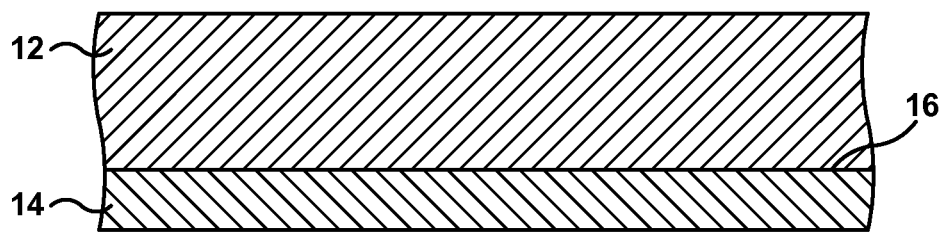
FIG. 1 is a cross-sectional diagram illustrating an example of an antimicrobial accessory including a first layer comprising a biocompatible polymer, an antimicrobial, and an antioxidant, and an adhesive layer formed on the first layer.

In general, the disclosure is directed to an antimicrobial accessory that may be implanted in a body of a patient. The patient may be, but will not always be, a human. In some examples, the antimicrobial accessory may be configured to be implanted proximate to or attached to an implantable medical device (IMD). For example, the antimicrobial accessory may be utilized with an implantable cardioverter/defibrillator, a pacemaker, an implantable drug delivery device, an implantable monitoring device that monitors one or more physiological parameter of a patient, an implantable neurostimulator (e.g., a spinal cord stimulator, a deep brain stimulator, a pelvic floor stimulator, a peripheral nerve stimulator, or the like), a cardiac or neurological lead, a catheter, an orthopedic device such as a spinal device, or the like. In general, the antimicrobial accessory may be attached to or implanted proximate to any medical device configured to be implanted in a body of a patient.

In other examples, the antimicrobial accessory may be formed integrally with the IMD. For example, the antimicrobial accessory may form a portion of a housing of an IMD, or may form a portion of a lead body or catheter body. In any of these examples, the antimicrobial accessory may reduce or substantially eliminate risk of infection proximate to an implant site at which the antimicrobial accessory is implanted in a body of a patient. The antimicrobial accessory may include a polymer, an antimicrobial, and an antioxidant.

Because the antimicrobial accessory is configured to be implanted in a body of a patient, the antimicrobial accessory may be sterilized after being formed and prior to being packaged or prior to being implanted in the patient. The antimicrobial accessory may be sterilized using, for example, ethylene oxide, an electron beam, a gamma beam, autoclaving, or the like. In some examples, a method of sterilization may initiate degradation of the polymer from which the antimicrobial accessory is formed, which may adversely affect the mechanical properties of the polymer. In some examples, the method of sterilization may adversely affect the antimicrobial in addition or alternative to affecting the polymer. The antimicrobial accessory includes an antioxidant to combat the degradation of the polymer and/or antimicrobial. The antioxidant may be more easily oxidized than the polymer and/or the antimicrobial, and may reduce or substantially prevent the oxidation of the polymer and/or the antimicrobial. For example, the antioxidant, when oxidized, may form a relatively stable free radical, which has a significantly lower reactivity than a free radical formed by reaction of the polymer or antimicrobial. As another example, the antioxidant, when oxidized, may form a compound that is not a free radical, and which is relatively non-reactive. In this way, even if the sterilization process initiates oxidation of the polymer or antimicrobial, the antioxidant may react with the oxidized polymer or antimicrobial and slow or substantially stop propagation of oxidation reactions. Alternatively or additionally, the antioxidant may react with and be oxidized by other free radical species or oxidizing species present in the antimicrobial accessory (e.g., a sterilization agent such as ethylene oxide) and may slow or substantially stop the oxidation of the polymer or antimicrobial.

In some examples, the antimicrobial and the antioxidant are mixed in the same layer of polymer to form a substantially homogeneous layer including the polymer, antimicrobial, and antioxidant. In other examples, the antimicrobial accessory includes at least three distinct layers. A first layer of the antimicrobial accessory may include a biodegradable polymer and an antimicrobial mixed in the biodegradable polymer. The antimicrobial accessory may further include a sacrificial diffusion layer formed on the first layer. The sacrificial diffusion layer may include a biodegradable polymer, which may be the same biodegradable polymer as in the first layer, or may be a different biodegradable polymer. The antimicrobial accessory may also include a topcoat including a biodegradable polymer and an antioxidant formed on the sacrificial diffusion layer. The sacrificial diffusion layer may substantially prevent mixing in the antimicrobial accessory of the antimicrobial and the antioxidant or a product of oxidation of the antioxidant.

FIG. 1 is a cross-sectional diagram of an example of an antimicrobial accessory 10 including a first layer 12 comprising a biocompatible polymer, an antimicrobial mixed in the biocompatible polymer, and an antioxidant mixed in the biocompatible polymer. In some examples, as illustrated in FIG. 1, antimicrobial accessory 10 further includes an adhesive layer 14 formed on a first surface 16 of the first layer 12. In other examples, antimicrobial accessory does not include adhesive layer 14.

In some examples, the biocompatible polymer is biodegradable or bioabsorbable, such that first layer 12 of antimicrobial accessory 10 breaks down or is absorbed by a body of a patient over time after being implanted in the patient. This may facilitate release of substantially all of the antimicrobial, which may reduce risk of bacteria developing resistance to the antimicrobial in antimicrobial accessory 10. An antimicrobial accessory 10 including a biodegradable polymer may also mitigate or prevent growth of bacteria on antimicrobial accessory 10 after the antimicrobial has eluted from the accessory 10. For example, the biodegradable polymer may break down over time after being implanted in the patient. In some examples, the biodegradable polymer may comprise poly(lactic-co-glycolic acid) (PLGA), poly(lactic acid)

(PLA), poly(glycolic acid) (PGA), poly(ethylene oxide) (PEO), poly(ortho ester) (POE), poly(dioxanone), a hydrophilic hydrogel, a hydrophobic hydrogel, a polyanhydride, an amino acid polymer such as a tyrosine polymer, or the like.

In other examples, the biocompatible polymer is not biodegradable and may remain implanted in the body of the patient indefinitely. For example, the polymer may include silicone, polyurethane, an epoxy, nylon, a polyester, blends of these polymers, co-copolymers of these polymers, or the like.

The antimicrobial may include, for example, an antibiotic such as minocycline, rifampin, clindamycin, tigecycline, daptomycin, gentamicin, or another fluoroquinolone, an antiseptic, an antimicrobial peptide, a quaternary ammonium, or the like. In some examples, the antimicrobial may be provided in a salt form, e.g., minocycline HCl. The antimicrobial may be selected to provide efficacious prevention or treatment of any infection which may be present proximate to the implant site at which the IMD is implanted. In some examples, the antimicrobial accessory may include at least two antimicrobials, and the combination of the at least two antimicrobials may be selected to efficaciously treat or prevent any infection present proximate to the implant site of the IMD. One example of two antimicrobials that may be used together is minocycline and rifampin.

In general, the antimicrobial may be mixed into first layer 12 to a concentration of less than about 50 weight percent (wt. %). In some preferred examples, the antimicrobial may be mixed into first layer 12 to a concentration of between about 5 wt. % and about 50 wt. %. In other preferred examples, the antimicrobial may be mixed into first layer 12 to a concentration of between about 10 wt. % and about 20 wt. %. The concentration to which the antimicrobial is mixed into first layer 12 may depend on, for example, the method of forming antimicrobial accessory 10, the efficacy of the antimicrobial, the geometry of antimicrobial accessory 10, the desired elution profile of the antimicrobial from antimicrobial accessory 10, the desired duration of elution of the antimicrobial from antimicrobial accessory 10, or the like.

The antioxidant may include, for example, a naturally occurring compound that possesses antioxidant properties. In other words, the compound is capable of mitigating or eliminating oxidation of other molecules, such as the polymer and/or antimicrobial in antimicrobial accessory 10. In many oxidation reactions, a free radical is formed as an intermediate in the oxidation reaction or as a product of the oxidation reaction. The antioxidant may react with the free radical and thus inhibit further reactions. In many cases, the antioxidant may contain one or more phenyl rings, conjugated double bonds, or carboxyl groups. In some examples, the antioxidant may be lipid soluble, may be a biological compound, or both.

In some examples, the antioxidant may include a compound that contains multiple conjugated double bonds, e.g., a highly conjugated compound, a relatively low molecular weight compound, or both. A highly conjugated compound may be a more effective antioxidant than a compound including fewer conjugated double bonds. When an antioxidant compound is highly conjugated and relatively low molecular weight, the antioxidant may be an efficient electron or free radical scavenger on a per weight basis. Additionally, an antioxidant with a relatively low molecular weight may facilitate mixing of the antioxidant into the polymer. Examples of antioxidants that are highly conjugated, relatively low molecular weight, or both are shown below in Formulas 1-5.

In some examples, the antioxidant includes an enzyme and a substrate on which the enzyme acts. The enzyme catalyzes oxidation of the substrate, and may provide improved oxidation protection to the polymer and/or antimicrobial than an antioxidant substrate alone. Examples of antioxidants including an enzyme and a substrate on which the enzyme acts are shown below in Reactions 1-3.

In one example, the antioxidant includes citric acid, also referred to as 3-hydroxypentanedioic acid-3-carboxylic acid. The structure of citric acid is shown in Formula. 1.

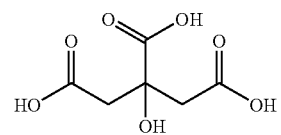

Formula 1

Citric acid contains three carboxyl groups, which may be oxidized by removal of a hydrogen atom. The resulting free radical is stabilized by resonance of the lone electron between the adjacent carbon-oxygen bonds. Citric acid has a molecular weight of approximately 192.12 g/mol.

In another example, the antioxidant includes maltol. Maltol includes conjugated double bonds, and has a molecular weight of approximately 126.11 g/mol. The structure of maltol is shown in Formula 2.

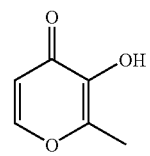

Formula 2

In another example, the antioxidant includes kojic acid, which also is referred to as 5-hydroxy-2-(hydroxymethyl)-4-pyrone or 2-hydroxymethyl-5-hydroxy-γ-pyrone. Kojic acid includes conjugated double bonds and has a molecular weight of approximately 142.11 g/mol. The chemical structure of kojic acid is shown below in Formula 3.

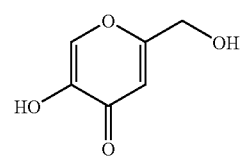

Formula 3

In another example, the antioxidant includes malic acid. The chemical structure of malic acid is shown below in Formula 4.

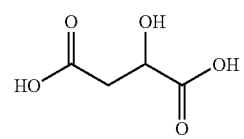

Formula 4

Malic acid includes two carboxyl groups that may be easily oxidized by removal of a hydrogen atom. The oxidized malic acid may be stabilized by resonance of the free electron between the adjacent carbon-oxygen bonds of the carboxyl groups. Malic acid has a molecular weight of approximately 134.09 g/mol.

The antioxidant may also include vitamin A, the structure of which is shown below in Formula 5. Vitamin A includes five of conjugated double bonds and has a molecular weight of approximately 286.45 g/mol.

Formula 5

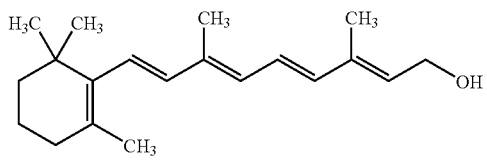

In some examples, the antioxidant includes an enzyme and a substrate antioxidant on which the enzyme acts. The use of an enzyme may catalyze the oxidation of the substrate antioxidant, and may increase the efficacy with which the substrate antioxidant protects the polymer and/or antimicrobial from oxidation.

In some examples, the antioxidant may include an ascorbate peroxidase (or APX1) in combination with an ascorbate. Ascorbate peroxidases are enzymes that detoxify peroxides using ascorbate as a substrate. Ascorbate peroxidases catalyze transfer of electrons from ascorbate to a peroxide. The transfer of the electrons produces dehydroascorbate and water. One such reaction catalyzed by ascorbate peroxidases is shown below in Reaction 1. In Reaction 1, ascorbate peroxidase catalyzes oxidation of ascorbic acid to dehydroascorbic acid and reduction of hydrogen peroxide to water. Ascorbate peroxidases may provide general antioxidant activities by catalyzing the reaction of ascorbate with other free radicals or free radical generating compounds in a similar manner.

Reaction 1

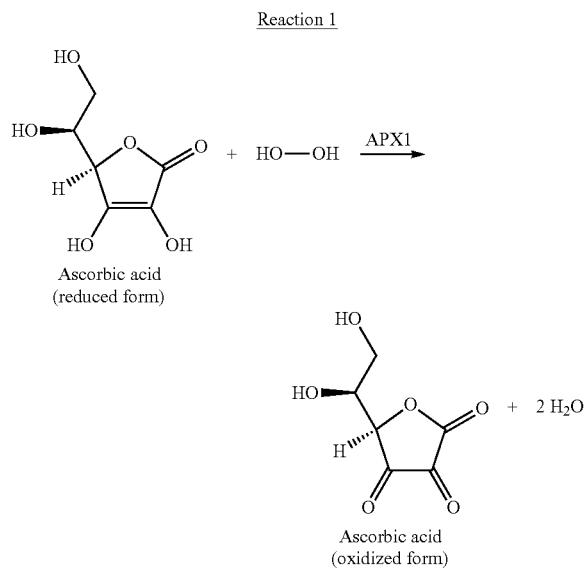

The antioxidant may also include a glutathione peroxidase in combination with a glutathione. Glutathione peroxidase is an enzyme family that reduces peroxides using glutathione as a substrate. One example of a reaction catalyzed by glutathione peroxidase is shown below in Reaction 2. Glutathione peroxidase may provide more general antioxidant activities by catalyzing the reaction of glutathione with other free radicals or free radical generating compounds in a similar manner.

Reaction 2

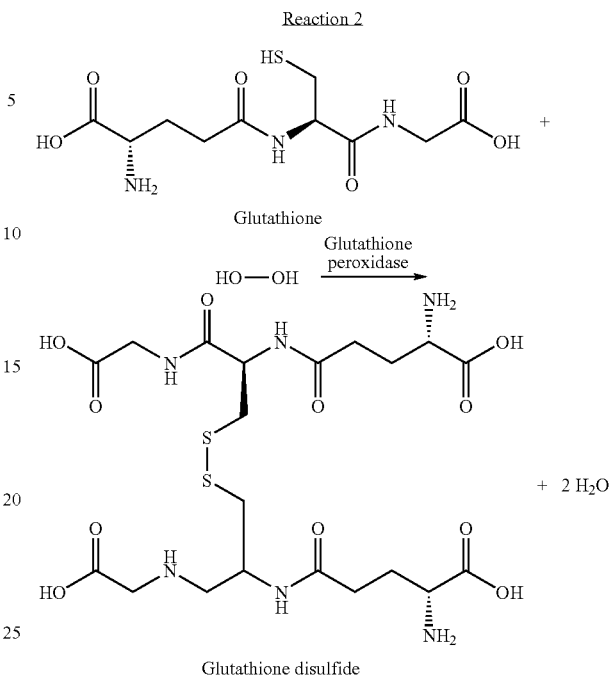

In some examples, the antioxidant may include a superoxide dismutase (SOD) and a metal, such as copper, manganese, iron, or nickel. Superoxide dismutases are enzymes that catalyze the dismutation of superoxide into oxygen and hydrogen peroxide using a metal substrate. The dismutation of superoxide may be represented as two half-reactions, shown below in Reaction 3.

$$M^{(n+1)+}\text{-SOD}+O_2^- \rightarrow M^{n+}\text{-SOD}+O_2$$

$$M^{n+}\text{-SOD}+O_2^-+2H^+ \rightarrow M^{(n+1)+}\text{-SOD}+H_2O_2 \quad \text{Reaction 3}$$

where M=Cu (n=1), Mn (n=2), Fe (n=2), or Ni (n=2).

Depending on the antioxidant used, antimicrobial accessory 10, and more specifically first layer 12, may include a range of antioxidant concentrations. In some examples, first layer 12 may include less than about 15 volume percent (vol. %) antioxidant. In other examples, first layer 12 may include less than about 9 vol. % antioxidant. In some preferred examples, first layer 12 may include between about 2 vol. % and about 9 vol. % antioxidant, or between about 5 vol. % and about 9 vol. % antioxidant. In examples in which the antioxidant includes both an enzyme and a substrate antioxidant, the combined concentration of the enzyme and substrate antioxidant in first layer 12 may be as great as about 30 vol. %. In some examples, the combined concentration of the enzyme and the substrate antioxidant in first layer may be as greater as about 15 vol. %. The amount of antioxidant in first layer 12 may be selected by considering, for example, a radiation level to which antimicrobial accessory 10 will be exposed, a desired shelf-life of antimicrobial accessory 10, a thickness of antimicrobial accessory 10, or which antioxidant is being used in antimicrobial accessory 10.

The polymer, antioxidant, and antimicrobial may be mixed in a solvent, such as tetrahydrofuran (THF) to form a solution or suspension. The solution or suspension may then be spray coated onto a substrate, such as a release liner, to form antimicrobial accessory 10. In other examples, the solution or suspension may be coated onto a release liner using another coating technique, such as, for example, knife coating, air knife coating, gap coating, gravure coating, slot die coating, metering rod coating, doctor blade, or the like.

In some examples, the antioxidant and/or the antimicrobial may be mixed directly into a polymer melt and extruded, casted, or molded to form antimicrobial accessory 10. In examples in which the antioxidant and/or antimicrobial is mixed into a polymer melt, the melt temperature, mixing shear rate, and residence time may be balanced to prevent degradation of the antimicrobial and/or antioxidant. For example, lower temperatures, shear rates, and/or residence times may reduce or substantially eliminate degradation of the antioxidant and/or antimicrobial. In various examples, one, two, or all three of the melt temperature, mixing shear rate, and residence time may be controlled or selected to mitigate or eliminate degradation of the antimicrobial and/or antioxidant.

In some examples, as illustrated in FIG. 1, antimicrobial accessory 10 includes a adhesive layer 14, such as, for example, a silicone, acrylic, or polyisobutylene PSA, applied on first surface 16 of first layer 12. Adhesive layer 14 may be applied to first surface 16 of first layer 12 by, for example, spray coating, knife coating, air knife coating, gap coating, gravure coating, slot die coating, metering rod coating, doctor blade, or the like.

In other examples, antimicrobial accessory 10 does not include an adhesive layer 14. For example, antimicrobial accessory 10 may be attached to an IMD by other means, such as a suture or staple. In other examples, antimicrobial accessory 10 is not be attached to an IMD in any manner, and is simply implanted in a patient proximate to an IMD. These methods may be advantageous when first layer 12 includes a biodegradable polymer, because no adhesive residue will be left on a surface of the IMD. In some examples, the suture may also be biodegradable. In other examples, antimicrobial accessory 10 may be formed integrally with a housing of an IMD, or may form a portion of a lead body, catheter, or the like. In such examples, antimicrobial accessory 10 may not include an adhesive layer 14 or any other means of attachment. Instead, antimicrobial accessory 10 may be a portion of the IMD, lead, or catheter.

In examples in which antimicrobial accessory 10 includes an adhesive layer 14, antimicrobial accessory 10 may be disposed on a release liner, such as a fluoropolymer release liner, to provide a convenient article for storing, shipping, and providing to the implanting clinician. In some examples, an antimicrobial accessory 10 disposed on a release liner may be packaged in a foil package or other substantially air and water impermeable package that is vacuum sealed or backfilled with an inert gas.

Antimicrobial accessory 10 may then be sterilized using, for example, an electron beam, a gamma beam, ethylene oxide, autoclaving, or the like. As described above, in some examples the sterilization may initiate degradation of one or both of the polymer and antimicrobial in antimicrobial accessory 10 through oxidation reactions. The presence of the antioxidant may slow or substantially stop the oxidation of the polymer and/or the antimicrobial.

Figure 2:
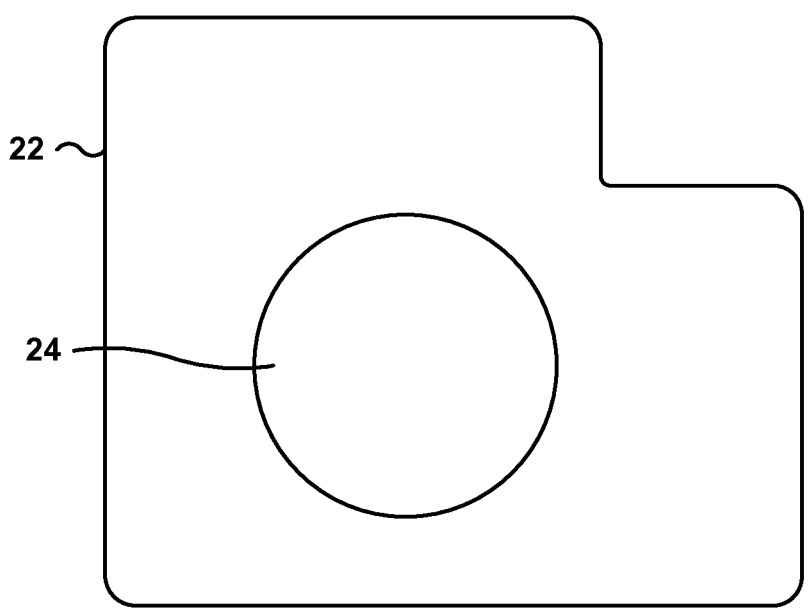
FIG. 2 is a conceptual diagram of an example of an antimicrobial accessory attached to a housing of an implantable medical device.

Antimicrobial accessory 10 may be formed into one of a variety of form factors, including, for example, a disk, a sheet, or a film. As illustrated in FIG. 2, an implantable system 20 may include an IMD 22 and a disk-shaped antimicrobial accessory 24. Disk-shaped antimicrobial accessory 24 may be adhered to a housing of IMD 22 by an adhesive layer (e.g., adhesive layer 14, FIG. 1), or may be attached to IMD 22 by a suture or staple. In some examples, disk-shaped antimicrobial accessory 24 may be sutured to a polymer connector block of IMD 22 or an aperture defined in the connector block. In other examples, antimicrobial accessory 10 may not be attached to IMD 22 in any manner, and may simply be implanted in a patient proximate to IMD 22. These non-adhesive attachment methods may be advantageous when disk-shaped antimicrobial accessory 24 includes a biodegradable polymer, because no adhesive residue will be left on a surface of IMD 22. In some examples, the suture may also be biodegradable.

An antimicrobial accessory also may be constructed in other, different form factors, such as an extruded cylinder, a paste, or a clip. In some examples, an antimicrobial accessory 26 may include a sheet or film, which may be adhered to IMD 22. The sheet, film, or disk-shaped antimicrobial accessory 24 may be applied to a single surface of IMD 22, or may be applied to two or more surfaces of IMD 22. The sheet or film may include a thickness similar to those described with respect to disk-shaped antimicrobial accessory 24. Further, the sheet or film may be manufactured by similar processes to disk-shaped antimicrobial accessory 24, and may be packaged and sterilized similarly.

Figure 3:
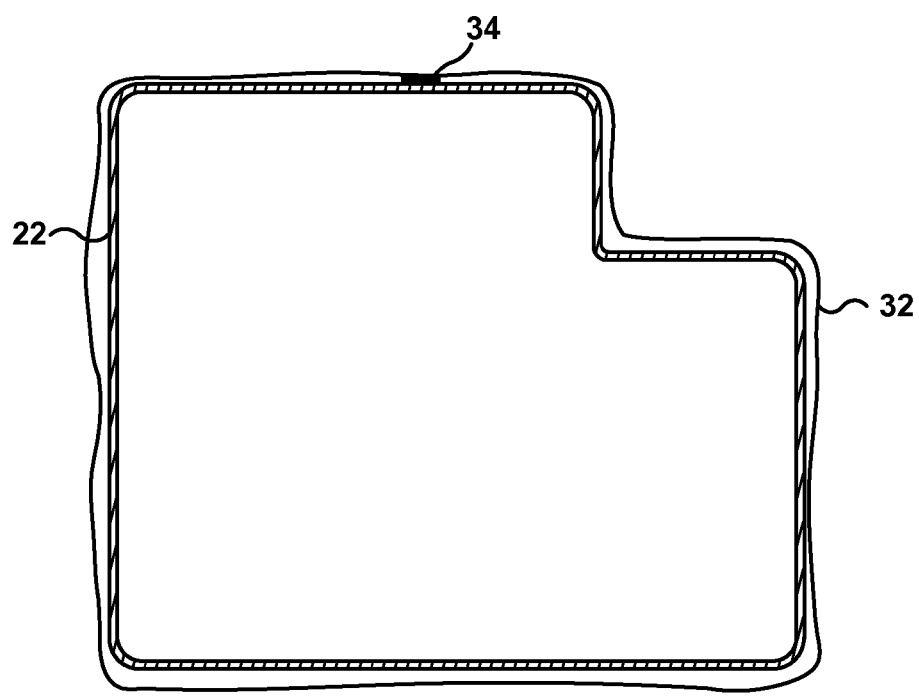
FIG. 3 is a conceptual diagram of an example of an antimicrobial accessory including a pouch enclosing an implantable medical device.

In other examples, as illustrated in FIG. 3, an antimicrobial accessory 32 includes a pouch 32 that at least partially encloses a housing of IMD 22. In the example illustrated in FIG. 3, pouch 32 substantially fully encloses the housing of IMD 22. As used herein, substantially fully enclosing refers to a pouch 32 that fully encloses the housing of IMD 22, but which may define at least one aperture that permits a lead, catheter, or other probe to extend from IMD 22 and out of pouch 32. In some examples, pouch 32 may be attached to the housing of IMD 22 by an adhesive 34. Adhesive 34 may also function to close an opening in pouch 32 through which IMD 22 is inserted into pouch 32. In other examples, pouch 32 simply fits around the housing of IMD 22. In some examples, the opening in pouch 32 through which IMD 22 is inserted may be closed by welding, melting, or adhering two portions of pouch 32 together to form a substantially continuous pouch 32. Pouch 32 may be sized and configured to fit intimately over the housing of IMD 22, or may be sized and configured to fit more loosely over the housing. In addition, pouch 32 may be customized for an individual IMD 22 or a type or class of IMD 22, or may be formed more generically and may fit over a wider range of IMDs.

Figure 4:
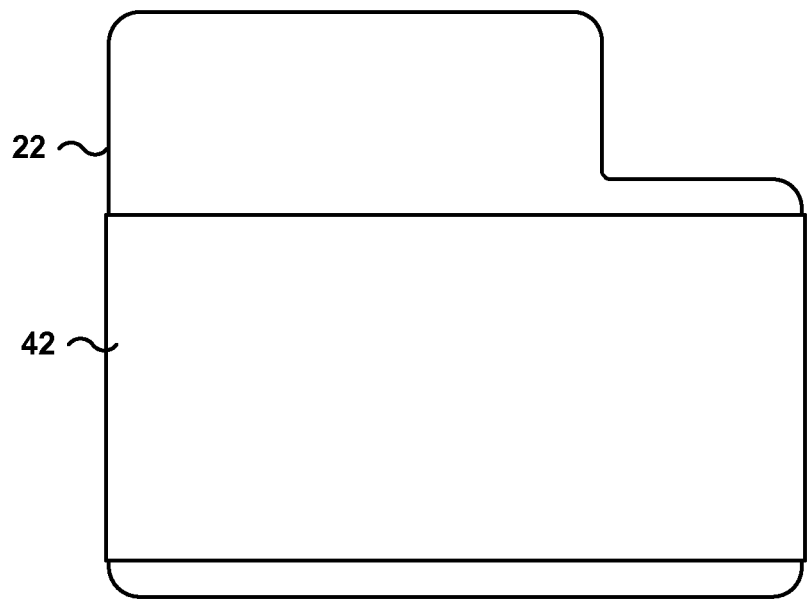
FIG. 4 is a conceptual diagram of an example of an antimicrobial accessory including a sleeve fitted around a housing of an implantable medical device.

In other examples, as illustrated in FIG. 4, an antimicrobial accessory may be formed into a sleeve 42. Sleeve 42 may be sized and configured to fit over a housing of the IMD 22. The antimicrobial sleeve 42 may include a polymer, an antioxidant, and at least one antimicrobial. In some examples, sleeve 42 may form a friction fit with the housing of the IMD 22, which maintains the sleeve substantially in position relative to the housing of IMD 22. Sleeve 42 may also be adhered to the IMD 22 by an adhesive, either additionally or instead of being friction fit around the housing.

Figure 5:
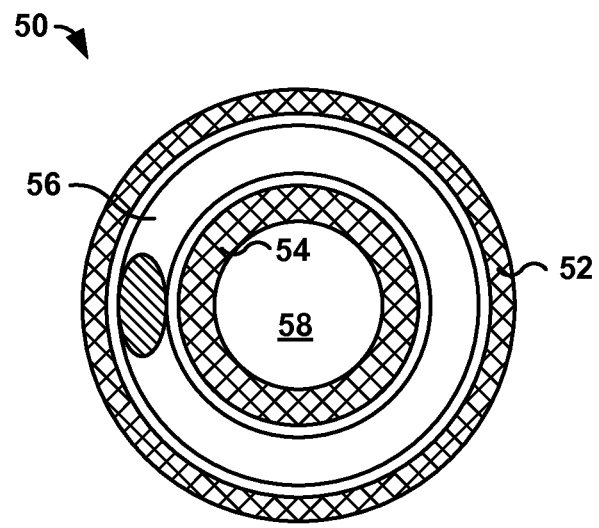
FIG. 5 is a cross sectional diagram of an example of a lead body including an outer jacket comprising an antimicrobial accessory.

An antimicrobial accessory also may be formed integral with an IMD, catheter, or lead body. For example, an antimicrobial accessory may form an integral portion of a catheter, a housing of an IMD, a polymeric connector block of an IMD, or the like. In other examples, as illustrated in FIG. 5, an antimicrobial accessory includes an antimicrobial sheath 52 that forms an integral portion of a lead body 50. FIG. 5 is a cross section of lead body 50, and also illustrates an inner sheath 54 that defines an inner lumen 58 through which a stylet may be introduced to stiffen and guide lead body 50 during implantation in a patient. Lead body 50 also includes a coiled conductor 56 disposed in an annulus formed between antimicrobial sheath 52 and inner sheath 54. In some examples, antimicrobial sheath 52 forms substantially the entire portion of an external sheath of the lead body 50, e.g., antimicrobial sheath 52 may extend substantially from a proximal end of lead body 50 to a distal end of lead body 50. In other examples, antimicrobial sheath 52 forms only a portion of an external sheath of the lead body 50, and lead body 50 includes an external sheath that includes at least one portion that is not an antimicrobial sheath 52, i.e., does not include an antimicrobial.

Although the preceding disclosure has been directed to an antimicrobial accessory including a single layer into which the antimicrobial and antioxidant are mixed, in some examples it may be beneficial to prevent mixing between the antimicrobial and the antioxidant (or products of the oxidation of the antioxidant). For example, the antioxidant may react to form impurities that negatively affect the efficacy of the antimicrobial. For this reason, an antimicrobial accessory may include in some examples a first layer comprising the antimicrobial, a sacrificial diffusion layer formed on a surface of the first layer, and a topcoat comprising the antioxidant formed on the sacrificial diffusion layer.

Figure 6:
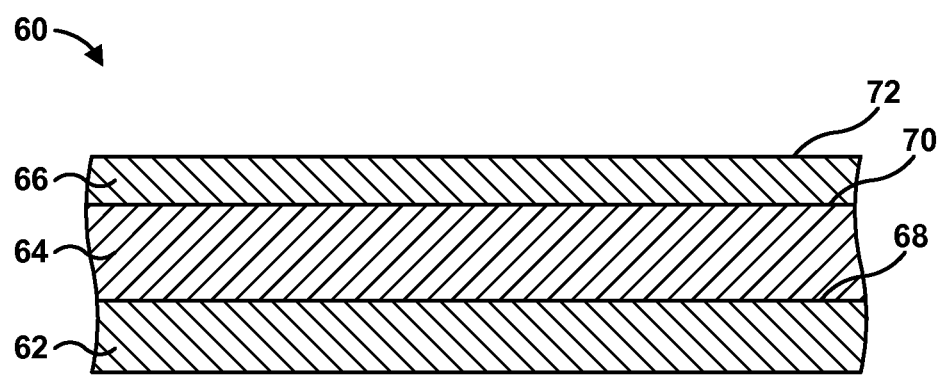
FIG. 6 is a cross-sectional diagram illustrating an example of an antimicrobial accessory including a first layer comprising a biodegradable polymer and an antimicrobial, a sacrificial diffusion layer comprising a biodegradable polymer formed on the first layer, and a topcoat comprising a biodegradable polymer and an antioxidant formed on the sacrificial diffusion layer.

FIG. 6 is a cross-sectional diagram that illustrates an example of such an antimicrobial accessory 60. Antimicrobial accessory 60 includes a first layer 62 including a first surface 68. A sacrificial diffusion layer 64 is formed on first surface 68 of first layer 62. Sacrificial diffusion layer 64 includes opposite first surface 68 a second surface 70, on which a topcoat 66 is formed.

Each of first layer 62, sacrificial diffusion layer 64, and topcoat 66 may be formed of a biocompatible, biodegradable polymer. For example, each of first layer 62, sacrificial diffusion layer 64, and topcoat 66 may be formed of at least one of poly(lactic-co-glycolic acid) (PLGA), poly(lactic acid) (PLA), poly(glycolic acid) (PGA), poly(ethylene oxide) (PEO), poly(ortho ester) (POE), poly(dioxanone), a hydrophilic hydrogel, a hydrophobic hydrogel, a polyanhydride, an amino acid polymer such as a tyrosine polymer, or the like. In some examples, at least two of first layer 62, sacrificial diffusion layer 64, and topcoat 66 are formed of the same polymer, while in other examples, each of first layer 62, sacrificial diffusion layer 64, and topcoat 66 are formed of different polymers.

First layer 62 may include an antimicrobial mixed into the biodegradable polymer. As described above, the antimicrobial may include at least one of minocycline, rifampin, clindamycin, tigecycline, daptomycin, gentamicin, or another fluoroquinolone, an antiseptic, an antimicrobial peptide, a quaternary ammonium, or the like. In some examples, the antimicrobial may be provided in a salt form, e.g., minocycline HCl. The antimicrobial may be selected to provide efficacious prevention or treatment of any infection that may be present proximate to the implant site at which the IMD is implanted. In some examples, the antimicrobial accessory includes at least two antimicrobials, and the combination of the at least two antimicrobials is selected to efficaciously treat or prevent any infection present proximate to the implant site of the IMD. One example of two antimicrobials that may be used together is minocycline and rifampin.

In general, first layer 62 may include less than about 50 wt. % of antimicrobial. In some preferred examples, first layer 62 includes between about 5 wt. % and about 50 wt. % of antimicrobial. In other preferred examples, first layer 62 includes between about 10 wt. % and about 20 wt. % of antimicrobial. The concentration of antimicrobial which first layer 62 includes may depend on, for example, the method of forming antimicrobial accessory 60, the efficacy of the antimicrobial, the geometry of antimicrobial accessory 60, the desired elution profile of the antimicrobial from antimicrobial accessory 60, the desired duration of elution of the antimicrobial from antimicrobial accessory 60, or the like.

In some examples, first layer 62 may not be exposed to the external environment, e.g., a bodily fluids, upon implantation of antimicrobial accessory 60 in the body of a patient. For example, first layer 62 may be an inner layer of an antimicrobial sheath 52 (FIG. 5), may be located adjacent to or attached to a housing of an IMD 22 (FIG. 2, 3, or 4), or may be oriented as an inner surface of a housing of a medical device. In such examples, first layer 62 may only be exposed to bodily fluids once topcoat 66 and sacrificial diffusion layer 64 degrade and are removed. This may serve to only allow release of the antimicrobial in first layer 62 through first surface 68.

Topcoat 66 may include an antioxidant mixed into a biodegradable polymer. In some examples, the antioxidant may include at least one of citric acid (3-hydroxypentanedioic acid-3-carboxylic acid), maltol, kojic acid (5-hydroxy-2-(hydroxymethyl)-4-pyrone or 2-hydroxymethyl-5-hydroxy-γ-pyrone), malic acid, or vitamin A. The antioxidant may also include an ascorbate peroxidase in combination with an ascorbate, a glutathione peroxidase in combination with glutathione, or a superoxide dismutase in combination with a metal such as Cu, Mn, Fe, or Ni.

Depending on the antioxidant used, topcoat 66 may include a range of antioxidant concentrations. In some examples, topcoat 66 may include less than about 15 vol. % antioxidant. In other examples, topcoat 66 may include less than about 9 vol. % antioxidant. In some preferred examples, topcoat 66 may include between about 2 vol. % and about 9 vol. % antioxidant, or between about 5 vol. % and about 9 vol. % antioxidant. In examples in which the antioxidant includes both an enzyme and a substrate antioxidant, the combined concentration of the enzyme and substrate antioxidant in topcoat 66 may be as great as about 30 vol. %. In some examples, the combined concentration of the enzyme and the substrate antioxidant in topcoat 66 may be as great as about 15 vol. %. The amount of antioxidant in topcoat 66 may be selected by considering, for example, a radiation level to which antimicrobial accessory 60 will be exposed, a desired shelf-life of antimicrobial accessory 60, a thickness of antimicrobial accessory 60, or which antioxidant is being used in antimicrobial accessory 60.

Sacrificial diffusion layer 64 may be formed of a biodegradable polymer that degrades over time after being implanted in a body of a patient. At least one of the biodegradable polymer and the thickness of sacrificial diffusion layer 64 may be selected to substantially prevent interdiffusion (i.e., mixing) of the antioxidant or products of oxidation of the antioxidant and the antimicrobial in sacrificial diffusion layer 64 (e.g., prior to degradation and removal of sacrificial diffusion layer 64).

Figure 7:
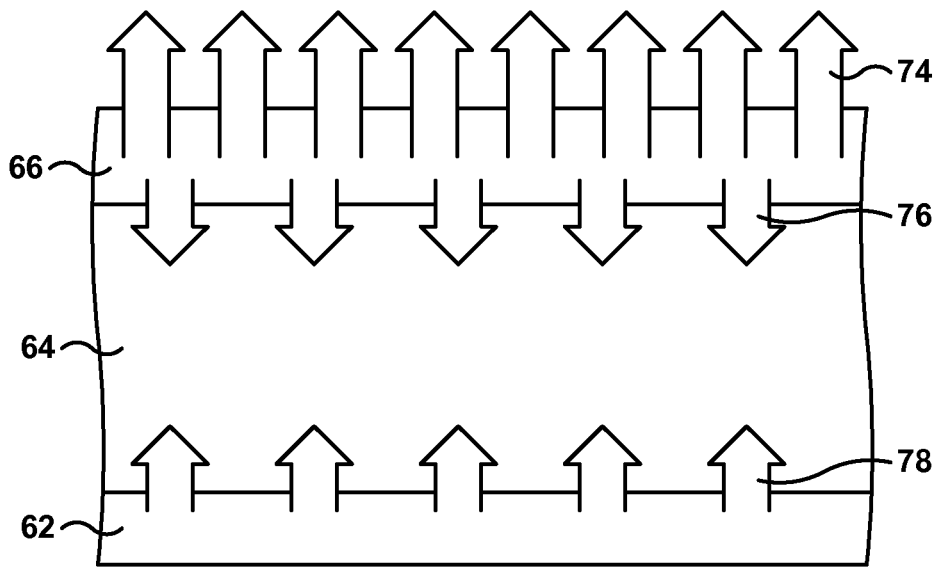
FIG. 7 is a conceptual diagram illustrating an example of diffusion of an antimicrobial out of a first layer and into a sacrificial diffusion layer, and diffusion of an antioxidant out of a topcoat and into the sacrificial diffusion layer and the surrounding environment.

As illustrated in FIG. 7, the antimicrobial may diffuse from first layer 62 into sacrificial diffusion layer 64. The diffusion of the antimicrobial from first layer 62 is represented by a first set of arrows 78. Similarly, the antioxidant or product of oxidation of the antioxidant may diffuse from topcoat 66 into sacrificial diffusion layer 64, as represented by a second set of arrows 76. The antioxidant or product of oxidation of the antioxidant may also diffuse from topcoat 66 into the surrounding environment, as represented by a third set of arrows 74.

Sacrificial diffusion layer 64 may function to substantially prevent diffusion of the antioxidant and antimicrobial from proceeding to the extent that the antioxidant and the antimicrobial mix in the sacrificial diffusion layer 64. More particularly, the thickness and/or material from which sacrificial diffusion layer 64 is formed may be selected so that topcoat 66 and sacrificial diffusion layer 64 degrade before mixing of the antioxidant and antimicrobial occurs in sacrificial diffusion layer 64.

The material from which sacrificial diffusion layer 64 is formed may affect the rate at which the antioxidant and the antimicrobial diffuses into and through sacrificial diffusion layer 64. Different materials may have different permeabilities to the antioxidant and the antimicrobial. By forming sacrificial diffusion layer 64 of a material that has a lower permeability to at least one of the antimicrobial and the antioxidant, the rate at which the antimicrobial and/or the antioxidant diffuses through sacrificial diffusion layer 64 may be lowered. This may more effectively prevent mixing of the antioxidant and antimicrobial than a material with a higher permeability to at least one of the antimicrobial and the antioxidant.

The material from which sacrificial diffusion layer 64 is formed may also affect the rate at which the sacrificial diffusion layer 64 degrades once implanted in the body of the patient. Thus, the selection of the material for forming sacrificial diffusion layer 64 may be based on consideration of the permeability of the material to the antimicrobial and/or antioxidant being used, and also the degradation rate of the material.

The thickness of sacrificial diffusion layer 64 may also affect the efficacy of the sacrificial diffusion layer 64 in preventing mixing of the antimicrobial and antioxidant. In particular, although a thicker sacrificial diffusion layer 64 may take a longer time to fully degrade, the thicker sacrificial diffusion layer 64 may emphasize a difference between the degradation rate and diffusion rates of the antimicrobial and/or the antioxidant. When the degradation rate of sacrificial diffusion layer 64 is faster than the diffusion rate of the antioxidant and/or the antimicrobial, an increase in the thickness of the layer 64 serves to increase the total time over which diffusion and degradation will occur in the layer 64, and thus lead to a greater difference in the progression of degradation of the layer 64 and diffusion of the antimicrobial and/or the antioxidant through the layer 64. In this way, a thicker sacrificial diffusion layer 64 may in some examples better prevent mixing of the antioxidant and the antimicrobial in the layer 64.

The thickness and/or composition of sacrificial diffusion layer 64 may also affect the release profile of the antimicrobial from first layer 62 into the body of a patient. In some examples, the antimicrobial will not be released into the body until the topcoat 66 and sacrificial diffusion layer 64 have degraded to the point that polymer including the antimicrobial mixed therein is exposed to the surrounding body environment. The polymer may include a portion of sacrificial diffusion layer 64 into which the antimicrobial has diffused, or may include first layer 62 if sacrificial diffusion layer 64 has degraded before substantial diffusion of the antimicrobial into sacrificial diffusion layer 64 has occurred. Because of this, the time required for degradation of topcoat 66 and sacrificial diffusion layer 64 to degrade to expose the antimicrobial to the surrounding environment may affect the release profile of the antimicrobial.

In some examples, the thickness of sacrificial diffusion layer 64 may be defined with reference to a thickness of first layer 62. For example, the thickness of sacrificial diffusion layer 64 may be between 0.5 times as thick and 5 times as thick as first layer 62. In other examples, sacrificial diffusion layer 64 may be thinner than 0.5 times as thick as first layer 62 (i.e., less than half as thick as first layer 62) or greater than 5 times as thick as first layer 62.

In some examples, in order to hasten the release of the antimicrobial, material may be selectively removed from topcoat 66 and, optionally, sacrificial diffusion layer 64 to form channels in the topcoat 66 and, optionally, the sacrificial diffusion layer 64. The channels may hasten release of the antimicrobial by increasing the degradation rate of the topcoat 66 and/or sacrificial diffusion layer 64 by increasing the surface area exposed to the external environment (e.g., bodily fluids). In some embodiments, the channels may also provide paths for bodily fluids to contact first layer 62 immediately after implant, which may facilitate release of the antimicrobial prior to degradation and removal of topcoat 66 and sacrificial diffusion layer 64. In some examples, the material in topcoat 66 and, optionally, sacrificial diffusion layer 64 may be removed by laser ablation, selective chemical etching, or the like. In other examples, the channels may be formed in topcoat 66 and, optionally, sacrificial diffusion layer 64 during formation of antimicrobial accessory 60 by, for example, molding, casting, or the like.

The release profile of the antimicrobial may also be affected by selection of the biodegradable polymer from which first layer 62 is formed. As described above, certain biodegradable polymers may permit faster diffusion of the antimicrobial, which may lead to a faster release of the antimicrobial once first layer 62 is exposed to the surrounding environment. For example, forming first layer 62 of hydrogel may lead to relatively fast release, or burst release, of the antimicrobial from first layer 62. Other biodegradable polymers may slow diffusion of the antimicrobial, which may lead to slower release of the antimicrobial once first layer 62 is exposed to the surrounding environment. By selecting appropriate materials for first layer 62 and sacrificial diffusion layer 64, control may be exercised over the release of antimicrobial from antimicrobial accessory 60.

Figure 8:
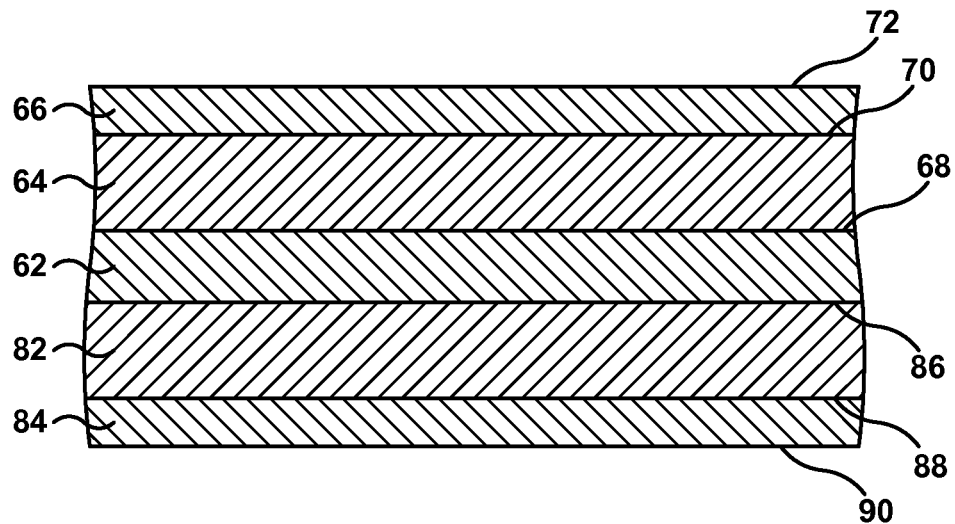
FIG. 8 is a cross-sectional diagram illustrating another example of an antimicrobial accessory including a first layer, a first sacrificial diffusion layer formed on a first surface of the first layer, a topcoat formed on the first sacrificial diffusion layer, a second sacrificial diffusion layer formed on a second surface of the first layer, and a base layer formed on the second sacrificial diffusion layer.

In some examples, as illustrated in FIG. 8, an antimicrobial accessory 80 may include more than three layers. For example, in addition to first layer 62, a first sacrificial diffusion layer 64, and topcoat 66, antimicrobial accessory 80 may include a second sacrificial diffusion layer 82 formed on a second surface 86 of first layer 62 and a base layer 84 formed on a surface 88 of second sacrificial diffusion layer 82.

In some examples, base layer 84 may comprise a biodegradable polymer and an antioxidant, similar to topcoat 66. As described above, the biodegradable polymer may comprise, for example, poly(lactic-co-glycolic acid) (PLGA), poly(lactic acid) (PLA), poly(glycolic acid) (PGA), poly(ethylene oxide) (PEO), poly(ortho ester) (POE), poly(dioxanone), a hydrophilic hydrogel, a hydrophobic hydrogel, a polyanhydride, an amino acid polymer such as a tyrosine polymer, or the like. In some examples, topcoat 66 and base layer 84 may include the same biodegradable polymer, while in other examples, topcoat 66 and base layer 84 may include different biodegradable polymers. The antioxidant in base layer 84 may include, for example, at least one of citric acid, maltol, kojic acid, malic acid, or vitamin A. In some examples, the antioxidant may include an enzyme and an antioxidant substrate, such as ascorbate peroxidase in combination with ascorbic acid, a glutathione peroxidase in combination with glutathione, or a superoxide dismutase in combination with a metal such as Ni, Cu, Mn, or Fe. The antioxidant in base layer 84 may be the same or different than the antioxidant in topcoat 66.

In other examples, base layer 84 may comprise an adhesive, and may be configured to adhere antimicrobial accessory 80 to a housing of an IMD (e.g., IMD 22 shown in FIG. 2, 3, or 4), a catheter body, a lead body, or a connector block of an IMD. The adhesive may be a pressure sensitive adhesive (PSA), such as a silicone, acrylic, or polybutadiene PSA. Base layer 84 including an adhesive may be applied to surface 88 of second sacrificial diffusion layer 82 by, for example, spray coating, knife coating, air knife coating, gap coating, gravure coating, slot die coating, metering rod coating, doctor blade, or the like.

Second sacrificial diffusion layer 82 may function similar to first sacrificial diffusion layer 64, and may substantially prevent diffusion of antimicrobial in first layer 62 into base layer 84, or may substantially prevent mixing of the antimicrobial and the antioxidant in base layer 84. Second sacrificial diffusion layer 82 may comprise a biodegradable polymer, such as, for example, poly(lactic-co-glycolic acid) (PLGA), poly(lactic acid) (PLA), poly(glycolic acid) (PGA), poly(ethylene oxide) (PEO), poly(ortho ester) (POE), poly(dioxanone), a hydrophilic hydrogel, a hydrophobic hydrogel, a polyanhydride, an amino acid polymer such as a tyrosine polymer, or the like. Second sacrificial diffusion layer 82 may comprise the same polymer as first sacrificial diffusion layer 64 or may comprise a different polymer than first sacrificial diffusion layer 64.

Figure 9:
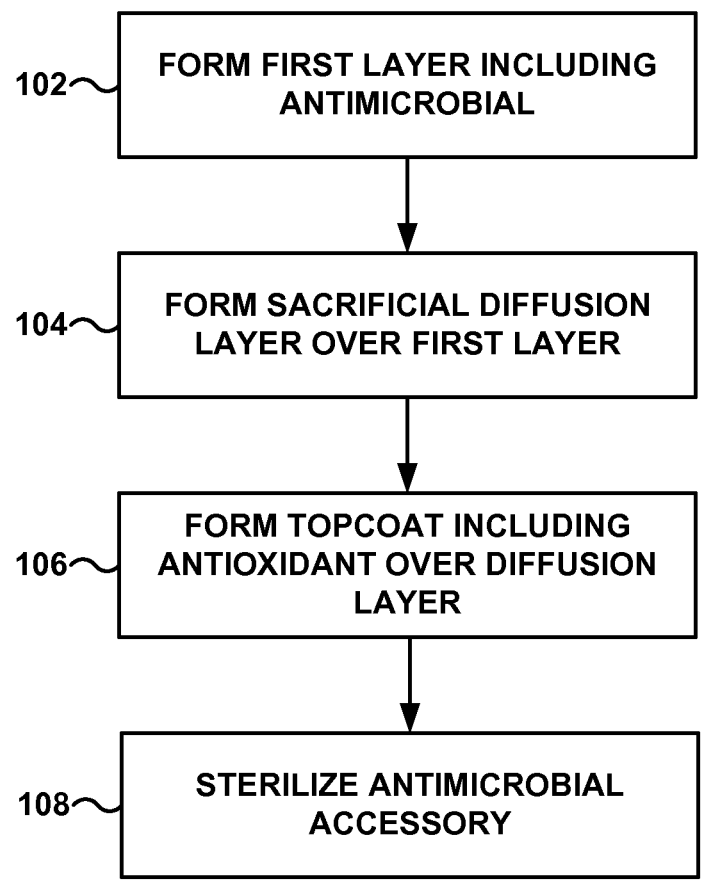
FIG. 9 is a flow diagram illustrating an example of a technique for forming an antimicrobial accessory including a first layer, a sacrificial diffusion layer formed on the first layer, and a topcoat formed on the sacrificial diffusion layer.

FIG. 9 is a flow diagram of an exemplary method of forming an antimicrobial accessory, which will be described with concurrent reference to antimicrobial accessory 60 depicted in FIG. 6. Initially, first layer 62 including a biodegradable polymer and an antimicrobial may be formed (102).

First layer 62 may be formed by mixing the biodegradable polymer and the antimicrobial in a solvent, such as tetrahydrofuran (THF) to form a solution or suspension. The solution or suspension may then be spray coated onto a substrate, such as a release liner, to form first layer 62. In other examples, the solution or suspension may be coated onto a release liner using another coating technique, such as, for example, knife coating, air knife coating, gap coating, gravure coating, slot die coating, metering rod coating, doctor blade, or the like.

In some examples, the antimicrobial may be mixed directly into a melt of the biodegradable polymer and the melt blend may be extruded, casted, or molded to form first layer 62. In examples in which the antimicrobial is mixed into a melt of the biodegradable polymer, the melt temperature, mixing shear rate, and residence time must be balanced to prevent degradation of the antimicrobial. For example, lower temperatures, shear rates, and residence times may reduce or substantially eliminate degradation of the antimicrobial. In various examples, one, two, or all three of the melt temperature, mixing shear rate, and residence time may be controlled or selected to mitigate or eliminate degradation of the antimicrobial.

In other examples, first layer 62 may initially be formed as a layer including substantially only the biodegradable polymer. The layer may be formed by, for example, extrusion, casting, molding, spray coating, knife coating, air knife coating, gap coating, gravure coating, slot die coating, metering rod coating, doctor blade coating, or the like. The first layer 62 including substantially only the biodegradable polymer may then be submerged in a solution or suspension of the antimicrobial in a solvent, such as THF. Submersion of the biodegradable polymer in the solution or suspension may result in impregnation of the polymer with the antimicrobial. The solvent may then be removed by a drying process, such as, for example, vacuum drying.

Once the first layer 62 is formed, the sacrificial diffusion layer 64 may be formed on first surface 68 of first layer 62 (104). As described above, in some examples, sacrificial diffusion layer 64 may comprise the same biodegradable polymer as first layer 62. In other examples, sacrificial diffusion layer 64 may comprise a different biodegradable polymer than first layer 62.

Sacrificial diffusion layer 64 may be formed on first layer 62 by a variety of processes. For example, the biodegradable polymer from which sacrificial diffusion layer 64 is formed may be dissolved in a solvent and coated on first layer using spray coating, knife coating, air knife coating, gap coating, gravure coating, slot die coating, metering rod coating, doctor blade coating, or the like. Sacrificial diffusion layer 64 may also be extruded onto first layer 62, or molded or casted onto first layer 62.

Next, the topcoat 66 may be formed on the sacrificial diffusion layer 64 (106). Topcoat 66 may include a biodegradable polymer and an antioxidant, as described above. In some examples, topcoat 66 may comprise the same biodegradable polymer as at least one of first layer 62 and sacrificial diffusion layer 64. In other examples, topcoat 66 may comprise a different biodegradable polymer than first layer 62 and sacrificial diffusion layer 64.

In some examples, topcoat 66 may be formed by first mixing the biodegradable polymer and the antioxidant in a solvent, such as tetrahydrofuran (THF) to form a solution or suspension. The solution or suspension may then be spray coated onto sacrificial diffusion layer 64 to form topcoat 66. In other examples, the solution or suspension may be coated onto sacrificial diffusion layer 64 using another coating technique, such as, for example, knife coating, air knife coating, gap coating, gravure coating, slot die coating, metering rod coating, doctor blade, or the like.

In some examples, the antioxidant may be mixed directly into a melt of the biodegradable polymer and the melt blend may be extruded, casted, or molded onto sacrificial diffusion layer 64 to form topcoat 66. In examples in which the antimicrobial is mixed into a melt of the biodegradable polymer, the melt temperature, mixing shear rate, and residence time must be balanced to prevent degradation of the antioxidant. For example, lower temperatures, shear rates, and residence times may reduce or substantially eliminate degradation of the antioxidant. In various examples, one, two, or all three of the melt temperature, mixing shear rate, and residence time may be controlled or selected to mitigate or eliminate degradation of the antioxidant.

In other examples, topcoat 66 may initially be formed on sacrificial diffusion layer 64 as a layer including substantially only the biodegradable polymer. The layer may be formed by, for example, extrusion, casting, molding, spray coating, knife coating, air knife coating, gap coating, gravure coating, slot die coating, metering rod coating, doctor blade coating, or the like. The topcoat 66 including substantially only the biodegradable polymer may then be submerged in or washed with a solution or suspension of the antimicrobial in a solvent, such as THF. Submersion or washing of the biodegradable polymer in the solution or suspension may result in impregnation of the polymer with the antimicrobial. The solvent may then be removed by a drying process, such as, for example, vacuum drying, leaving a topcoat 66 that includes a biodegradable polymer mixed with or impregnated with the antioxidant.

Once antimicrobial accessory 60 has been formed, the accessory 60 may be sterilized (108). In some examples, antimicrobial accessory 60 may be sterilized prior to being packaged, while in other examples, antimicrobial accessory 60 may be sterilized after being packaged. Antimicrobial accessory 60 may be sterilized using, for example, an electron beam, a gamma beam, ethylene oxide, autoclaving, or the like. As described above, in some examples the sterilization may initiate degradation of one or both of the polymer and antimicrobial in antimicrobial accessory 60. The presence of the antioxidant in topcoat 66 may slow or substantially stop the oxidation of the polymer and/or the antimicrobial.

Antimicrobial accessory 60 may be packaged in a foil package or other substantially air and water impermeable package that is vacuum sealed or backfilled with an inert gas.

Antimicrobial accessory 60 may be provided to the implanting physician in different ways. For example, antimicrobial accessory 60 may be provided alone, and may be configured to be used with a variety of IMDs, such as different models of ICDs, pacemakers, drug delivery devices, neurostimulators, or monitoring devices. The implanting physician may determine that a patient may benefit from antimicrobial accessory 60 and may attach antimicrobial accessory 60 to an IMD prior to implanting the IMD in the patient.

In other examples, antimicrobial accessory 60 may be bundled together in a kit with an IMD, but may be provided physically separately from the IMD, e.g., may require the implanting clinician to attach antimicrobial accessory 60 to the IMD before implantation. This may provide convenience of having an antimicrobial accessory 60 provided with an IMD, but may still permit an implanting clinician to elect if he or she wishes to utilize the antimicrobial accessory 60 on a patient-by-patient basis.

In other examples, an IMD may be provided to the implanting clinician with antimicrobial accessory 60 already attached. This may provide the most straightforward implementation, as the implanting physician is not required to decide whether the antimicrobial accessory 60 is desired, and does not need to attach antimicrobial accessory 60 to the IMD prior to implanting the IMD in the patient.

Although certain features of the antioxidants, antimicrobials, polymer, or antimicrobial accessories have been described with reference to different Figures or examples within this disclosure, the various features of the antioxidants, antimicrobials, polymer, or antimicrobial accessories may be used together in combinations other than explicitly described herein. Other combinations of such features will be apparent to one of ordinary skill, and are within the scope of the following claims.

Various examples have been described in the disclosure. These and other examples are within the scope of the following claims.

The invention claimed is:

1. An antimicrobial accessory comprising:
   a first layer comprising a first biodegradable polymer and an antimicrobial;
   a sacrificial diffusion layer formed on the first layer, wherein the sacrificial diffusion layer comprises a second biodegradable polymer; and
   a topcoat formed on the sacrificial diffusion layer, wherein the topcoat comprises a third biodegradable polymer and an antioxidant, wherein the topcoat defines a plurality of channels formed in the topcoat, wherein the plurality of channels extend from an outer surface of the topcoat to the sacrificial diffusion layer, and wherein the sacrificial diffusion layer is configured to substantially prevent mixing of the antioxidant and the antimicrobial in the sacrificial diffusion layer due to diffusion of the antioxidant from the topcoat into the sacrificial diffusion layer and diffusion of the antimicrobial from the first layer into the sacrificial diffusion layer.

2. The antimicrobial accessory of claim 1, wherein the antioxidant is selected from the group consisting of citric acid, maltol, kojic acid, malic acid, vitamin A, an ascorbate peroxidase in combination with ascorbic acid, a glutathione peroxidase in combination with glutathione, a superoxide dismutase in combination with a metal, or combinations thereof.

3. The antimicrobial accessory of claim 1, wherein the antimicrobial is selected from the group consisting of minocycline, rifampin, clindamycin, tigecycline, daptomycin, gentamicin, another fluoroquinolone, an antiseptic, an antimicrobial peptide, a quaternary ammonium, or combinations thereof.

4. The antimicrobial accessory of claim 1, wherein at least one of the first biodegradable polymer, the second biodegradable polymer, and the third biodegradable polymer comprises a polymer selected from the group consisting of poly(lactic-co-glycolic acid), poly(lactic acid), poly(glycolic acid), poly(ethylene oxide), poly(ortho ester), poly(dioxanone) a hydrophilic hydrogel, a hydrophobic hydrogel, a polyanhydride, an amino acid polymer, or combinations thereof.

5. The antimicrobial accessory of claim 1, wherein at least two of the first biodegradable polymer, the second biodegradable polymer, and the third biodegradable polymer comprise the same biodegradable polymer.

6. The antimicrobial accessory of claim 1, wherein the first biodegradable polymer, the second biodegradable polymer, and the third biodegradable polymer each comprise a different biodegradable polymer.

7. The antimicrobial accessory of claim 1, wherein the sacrificial diffusion layer comprises a thickness of between approximately 0.5 times the thickness of the first layer and approximately 5 times the thickness of the first layer.

8. The antimicrobial accessory of claim 1, wherein the sacrificial diffusion layer comprises a plurality of channels extending from the topcoat to the first layer.

9. The antimicrobial accessory of claim 1, wherein the first layer comprises a first surface and a second surface, wherein the sacrificial diffusion layer comprises a first sacrificial diffusion layer and is formed on the first surface of the first layer, and wherein the antimicrobial accessory further comprises a second sacrificial diffusion layer formed on the second surface of the first layer and a base layer formed on the second sacrificial diffusion layer.

10. The antimicrobial accessory of claim 9, wherein the second sacrificial diffusion layer comprises a biodegradable polymer selected from the group consisting of poly(lactic-co-glycolic acid), poly(lactic acid), poly(glycolic acid), poly(ethylene oxide), poly(ortho ester), poly(dioxanone) a hydrophilic hydrogel, a hydrophobic hydrogen, a polyanhydride, an amino acid polymer, or combinations thereof.

11. The antimicrobial accessory of claim 9, wherein the base layer comprises a biodegradable polymer and an antioxidant.

12. The antimicrobial accessory of claim 11, wherein the biodegradable polymer is selected from the group consisting of poly(lactic-co-glycolic acid), poly(lactic acid), poly(glycolic acid), poly(ethylene oxide), poly(ortho ester), poly(dioxanone) a hydrophilic hydrogel, a hydrophobic hydrogen, a polyanhydride, an amino acid polymer, or combinations thereof.

13. The antimicrobial accessory of claim 11, wherein the antioxidant is selected from the group consisting of citric acid, maltol, kojic acid, malic acid, vitamin A, an ascorbate peroxidase in combination with ascorbic acid, a glutathione peroxidase in combination with glutathione, a superoxide dismutase in combination with a metal, or combinations thereof.

14. The antimicrobial accessory of claim 9, wherein the base layer comprises a pressure sensitive adhesive.

15. The antimicrobial accessory of claim 1, wherein the topcoat comprises less than approximately 9 vol. % antioxidant.

16. The antimicrobial accessory of claim 1, wherein the first layer comprises between approximately 10 wt. % antimicrobial and approximately 20 wt. % antimicrobial.

* * * * *